US011278189B2

(12) United States Patent
Tozzi et al.

(10) Patent No.: US 11,278,189 B2
(45) Date of Patent: *Mar. 22, 2022

(54) ENDOSCOPIC GUIDE INCLUDING ANCHORING HEAD THAT ACCOMMODATES A MAGNETIC OR FERROMAGNETIC AGENT

(71) Applicant: ENDOSTART S.R.L., Florence (IT)

(72) Inventors: Alessandro Tozzi, Florence (IT); Alberto Bruni, Florence (IT); Carlo Bruni, Empoli (IT)

(73) Assignee: ENDOSTART S.R.L., Florence (IT)

( * ) Notice: Subject to any disclaimer, the term of this patent is extended or adjusted under 35 U.S.C. 154(b) by 274 days.

This patent is subject to a terminal disclaimer.

(21) Appl. No.: 16/388,471

(22) Filed: Apr. 18, 2019

(65) Prior Publication Data

US 2019/0239727 A1 Aug. 8, 2019

Related U.S. Application Data

(63) Continuation-in-part of application No. 16/112,421, filed on Aug. 24, 2018, now Pat. No. 10,349,817.
(Continued)

(30) Foreign Application Priority Data

Jan. 12, 2017 (IT) .................... 102017000002679
Jan. 12, 2017 (IT) .................... 102017000002740

(51) Int. Cl.
*A61B 1/00* (2006.01)
*A61B 1/31* (2006.01)
(Continued)

(52) U.S. Cl.
CPC ...... *A61B 1/00158* (2013.01); *A61B 1/00082* (2013.01); *A61B 1/00154* (2013.01);
(Continued)

(58) Field of Classification Search
CPC ............ A61B 1/00158; A61B 1/00082; A61B 1/00154; A61B 1/31; A61M 25/0127; A61M 25/0158
See application file for complete search history.

(56) References Cited

U.S. PATENT DOCUMENTS 5,667,715 A * 9/1997 Foister .................... H01F 1/447
252/62.52
5,681,260 A 10/1997 Ueda et al.
(Continued)

FOREIGN PATENT DOCUMENTS

| JP | 08-89583 | 4/1996 |
| WO | WO 99/040957 | 8/1999 |
| WO | WO 2002/07794 | 1/2002 |

OTHER PUBLICATIONS

Machine Language translation of JP 408089583, Apr. 1996.*
(Continued)

*Primary Examiner* — John P Leubecker
(74) *Attorney, Agent, or Firm* — Knobbe Martens Olson & Bear, LLP

(57) ABSTRACT

An endoscopic guide includes a tubular guiding element and a magnetic field source. The tubular body element includes a body including a lumen, a longitudinal cavity, an anchoring head, and a magnetic or ferromagnetic agent. The anchoring head includes an endoscopic balloon. The magnetic or ferromagnetic agent is movable in the longitudinal cavity and configured to fill and empty the endoscopic balloon. The magnetic field source includes a permanent magnet.

21 Claims, 2 Drawing Sheets

Related U.S. Application Data which is a continuation of application No. PCT/IB2018/050164, filed on Jan. 11, 2018.

(51) Int. Cl.
*A61M 25/01* (2006.01)
*A61B 1/01* (2006.01)

(52) U.S. Cl.
CPC .................. *A61B 1/01* (2013.01); *A61B 1/31* (2013.01); *A61M 25/0127* (2013.01)

(56) References Cited

U.S. PATENT DOCUMENTS

| | | |
|---|---|---|
| 2002/0116043 A1 | 8/2002 | Garibaldi et al. |
| 2005/0154259 A1 | 7/2005 | DeMarco |
| 2007/0021731 A1 | 1/2007 | Garibaldi et al. |
| 2007/0265551 A1 | 11/2007 | Pfister |
| 2007/0270629 A1 | 11/2007 | Charles |
| 2010/0105984 A1 | 4/2010 | Brewer et al. |
| 2011/0285488 A1* | 11/2011 | Scott ..................... A61B 34/76 335/306 |
| 2012/0035460 A1 | 2/2012 | Stangenes et al. |
| 2018/0019049 A1* | 1/2018 | Lazarus ................ H01F 27/022 |
| 2018/0303504 A1 | 10/2018 | Eggert et al. |
| 2019/0000306 A1 | 1/2019 | Tozzi et al. |

OTHER PUBLICATIONS

International Search Report and Written Opinion issued in PCT Application No. PCT/IB2018/050164, dated Mar. 28, 2018, in 15 pages.

\* cited by examiner

ENDOSCOPIC GUIDE INCLUDING ANCHORING HEAD THAT ACCOMMODATES A MAGNETIC OR FERROMAGNETIC AGENT

INCORPORATION BY REFERENCE

The present application is a continuation-in-part of U.S. patent application Ser. No. 16/112,421, filed Aug. 24, 2018, which is a continuation of PCT Patent App. No. PCT/IB2018/050164, filed Jan. 11, 2018, each of which is hereby incorporated by reference in its entirety, and PCT Patent App. No. PCT/IB2018/050164 claims priority benefit of Italian Patent App. No. IT 102017000002740, filed on Jan. 12, 2017, and Italian Patent App. No. IT 102017000002679, filed on Jan. 12, 2017.

DESCRIPTION

The present invention relates to an endoscopic guide for catheters or endoscopes, in particular for flexible endoscopes.

Examples of such instruments are colonoscope, enteroscope, gastroscope, duodenoscope, echoendoscope, and the like.

BACKGROUND ART

The endoscopic guides (or "guidewire" in technical jargon) are used in the field to position and act, in fact, as a guide, in particular for a catheter, which is usually mounted sliding thereon; to this end, the catheter is provided with an operating channel in which the guide itself is placed in an assembled condition.

In the prior art, depending on the applications for which they are intended, various types of endoscopic guides are known.

A type of endoscopic guide provides an anchoring head which allows the guide to remain in place and acts as a support for the operations of the catheter or endoscope.

In some embodiments, for this purpose, the guides are provided with an inflatable balloon which, once introduced into the lumen of the organ and positioned, is inflated with air until it interferes with the walls of the lumen, thus remaining locked in place.

Although these guides with expandable anchoring head are used, they do however have some drawbacks.

In fact, these guides are "passive" in placing, i.e. they must be positioned manually by the medical operator and can be locked in place only when they are exactly at the desired point: in fact, if a small adaptation of their position is necessary, it would be necessary to deflate the balloon, position the head again and proceed with a new locking in place.

These operations require some time, which leads to additional discomfort for the patient.

Another limitation of some of these solutions is related to the fact that the lumen in which the guide head is placed is occluded: in the case of inflatable balloons, in particular, the occlusion is complete, while in the case of metal cages the occlusion is only partial, but only small passage areas between the segments of the cage remain available.

Moreover, such anchoring heads are difficult to be used in certain endoscopy fields, such as in the case of colonoscopy, due to the anatomical conformation of the organ in which the guide is introduced. In the colon, for example, the lumen diameter can range from 2-3 cm up to 6-8 cm in relation to the considered segment and to the presence or absence of pathological conditions or anatomical anomalies. This would imply the need for even very voluminous balloons.

Moreover, the anchoring through the balloons is obtained through the friction which is generated between the balloon and the surface of the organ mucosa. This implies that in order to obtain a more stable anchorage it is necessary to increase the pressure on the wall of the bowel, thereby extending the balloon further. However, this operation could result in excessive extension of the bowel, with the risk of causing pain or even tearing the tissue. Moreover, sometimes the bowel, especially in the elderly or in certain pathological conditions, may be dilated and flaccid to such an extent that it does not offer resistance to the balloon expansion. In this condition, the distension of the balloon can not only be risky, but is also ineffective.

However, obtaining a steady and stable anchoring is essential to ensure that the guide can also work for colonoscopes and in general endoscopes.

The colonoscope technique in particular requires special precautions for the introduction of the colonoscope to the terminal point of the colon, since the colon, in addition to having a twisted pattern, has flaccid walls whereby loops are formed which prevent the advance of the colonoscope tip and stretch the walls of the colon, thus causing the onset of pain and the risk of tearing the bowel: in these cases, the doctor must maneuver the instrument in an appropriate manner so as to rectify as much as possible the path and be able to proceed with the introduction of the colonoscope to the terminal point.

It should also be considered that the main difference between a colonoscope and a standard catheter is mass. As the mass of the catheter or the endoscope increases, a guide with higher stiffness is required. The rigidity of the guide derives mainly from two factors: the material it is made of and the force with which it is put in traction; the greater the pulling force, the larger the catheter mass. In order for the pulling force to be greater, it is necessary to achieve an anchoring as firm as possible.

The guides currently used in endoscopy cannot be constructed with particularly rigid material, as this could damage the bowel with the rigid tip.

In the case of anchoring with an inflatable balloon, when traction is exerted on the outer end of the guide during the above maneuvers, a traction not only of the guide is determined, but also of the balloon, of the bowel mucosa where the balloon is anchored and thus of the whole bowel and its ligaments. This sequence of events could lead to the onset of pain due to the traction of the visceral ligaments and damage to the mucosa. With these instruments, anchoring could also be ineffective.

In this regard, it should be noted that in the guides with inflatable balloon, the outer end of the guide is connected to an insufflator which regulates the pressure of the gas inside the balloon; this means that the outer end of the guide is not free, but engaged by the insufflator.

Even if, in principle, one could think of changing this anchoring area, there remains the limitation relating to the necessary presence of the insufflator, which has a certain cost and an additional encumbrance of the equipment, in addition to the necessary maintenance. Continuous control of the insufflation pressure is also required during use.

Another limitation of these solutions relates to the fact that an insufflator is not always available in every endoscopic room.

A common limitation of the known solutions of the prior art is also that it is not possible to remove the endoscope in use from the guide and replace it with another endoscope, keeping the guide in place; this is due to the fact that along the guide wire there are usually control devices which could hinder the extraction and therefore the replacement.

Yet another limitation of such solutions is related to the fact that it is generally appropriate for the dimensions of the anchoring or positioning head to be as small as possible, so as to be able to be easily introduced and maneuvered.

It should then be considered that, especially when the endoscopy consists of a colonoscopy, another limitation is related to locating the lesion (e.g. tumor, polyp or the like) by the operator. Locating is in fact of primary importance, for example to indicate to the surgeon in which segment of the colon there is a lesion which has been identified by the endoscopist during the colonoscopy. For example, it may happen that the endoscopist operator says that a polyp is in the descending colon, when it is in the sigmoid or in the transverse colon.

This happens because within the colon there are few points of reference, which induces even gross locating errors.

It is an object of the invention to provide an endoscopic guide for catheters or endoscopes which solves one or more of the technical problems described above. In this context, it is an object of the present invention to provide an endoscopic guide which is able to ensure a solid and less traumatic anchoring, in particular for use in colonoscopy.

It is another object of the invention to provide an endoscopic guide which allows to exert a significant pulling force on the guide itself.

It is a further object of the invention to provide an endoscopic guide which can also be used with large mass colonoscopes.

It is another object of the invention to provide an endoscopic guide which allows at least small movements of the anchoring head to be carried out when it is in the locked position, so as to avoid unnecessary activation/deactivation maneuvers.

It is another object of the invention to provide an endoscopic guide which allows the endoscope to be replaced while keeping the guide locked in place in the organ.

It is another object of the invention to provide an endoscopic guide which is relatively quick to be operated.

It is yet another object of the invention to provide an endoscopic guide which is relatively cost-effective and simple to be implemented.

It is another object of the invention to provide an endoscopic guide which is relatively safe even in case of malfunctions.

It is a further object of the invention to provide an endoscopic guide which allows to precisely locate possible lesions (e.g. tumors, polyps or the like), especially when the invention is used for a colonoscopy.

SUMMARY OF THE INVENTION

One or more of the tasks and objects described above and others which may become apparent later are achieved by an endoscopy system comprising an endoscopic guide, particularly for colonoscopes, comprising a tubular guiding element and an anchoring head, where the tubular guiding element comprises a longitudinal cavity, the anchoring head being provided at least with a container for accommodating a magnetic or ferromagnetic agent, the container being in communication with said longitudinal cavity, the endoscopic guide further comprising a magnetic or ferromagnetic agent movable in said longitudinal cavity for filling/emptying the container.

The magnetic or ferromagnetic agent comprises a magnetizable agent, i.e. an agent which reacts to the presence of an external magnetic field. The magnetic or ferromagnetic agent can be present in various forms, according to the preferred embodiment.

The invention further relates to an endoscopy system, preferably for colonoscopy, as defined in the appended claims, comprising an endoscopic guide according to the invention cooperating with a magnetic field source, where the magnetic field source is preferably associated with a device which is manually maneuverable, i.e. also without locomotion or assisted support devices. In certain embodiments, the manually maneuverable device is a handpiece in which the magnetic field source is movable between a working position and a safety or rest position, in which:

in the working position, the magnetic field source is close to the operating end of the handpiece, in the safety or rest position, the magnetic field source is remote from the operating end of the handpiece.

The invention further relates to a kit comprising an endoscopic guide according to the invention, a container of a ferromagnetic fluid in a predetermined amount, optionally a catheter, optionally a handpiece comprising a magnetic field source, optionally a syringe connectable to the endoscopic guide of the invention to introduce a ferromagnetic fluid.

The invention further relates to a method for introducing a colonoscope into a patient's colon which can be used for example for a diagnostic colonoscopy examination.

In particular, the invention relates to an endoscopy system, an endoscopic guide, an endoscopy kit and a colonoscopy method as outlined in the appended claims, the text of which forms an integral part of the present description.

Further features and advantages will become more apparent from the description of preferred but nonexclusive embodiments of the invention, shown by way of a non-limiting example.

DETAILED DESCRIPTION OF THE INVENTION

With reference to the figures, the invention will now be described in the various embodiments thereof.

Figure 1:
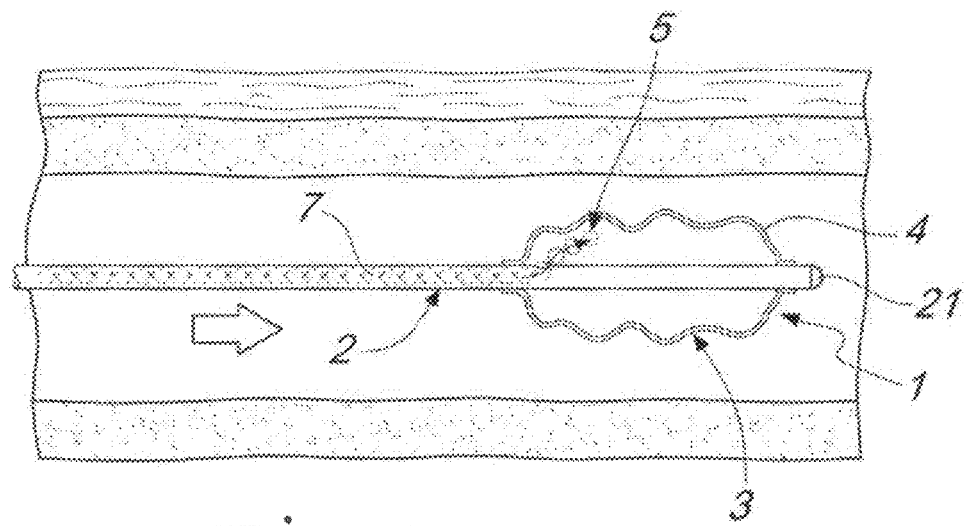
FIG. 1 is a sectional view of a first embodiment of a guide according to the invention.
Figure 2:
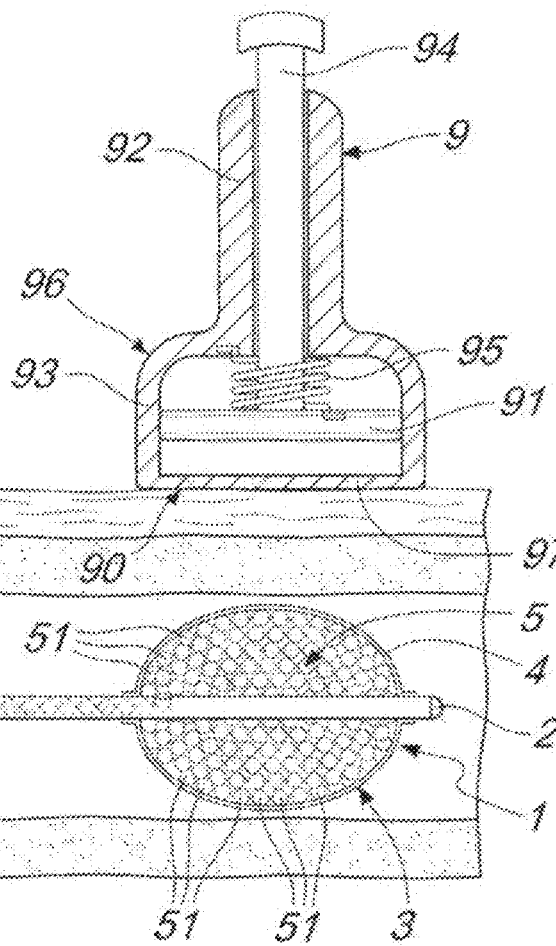
FIG. 2 is a sectional view of a first embodiment of an endoscopy system comprising the guide in FIG. 1, in a first operating condition.
Figure 3:
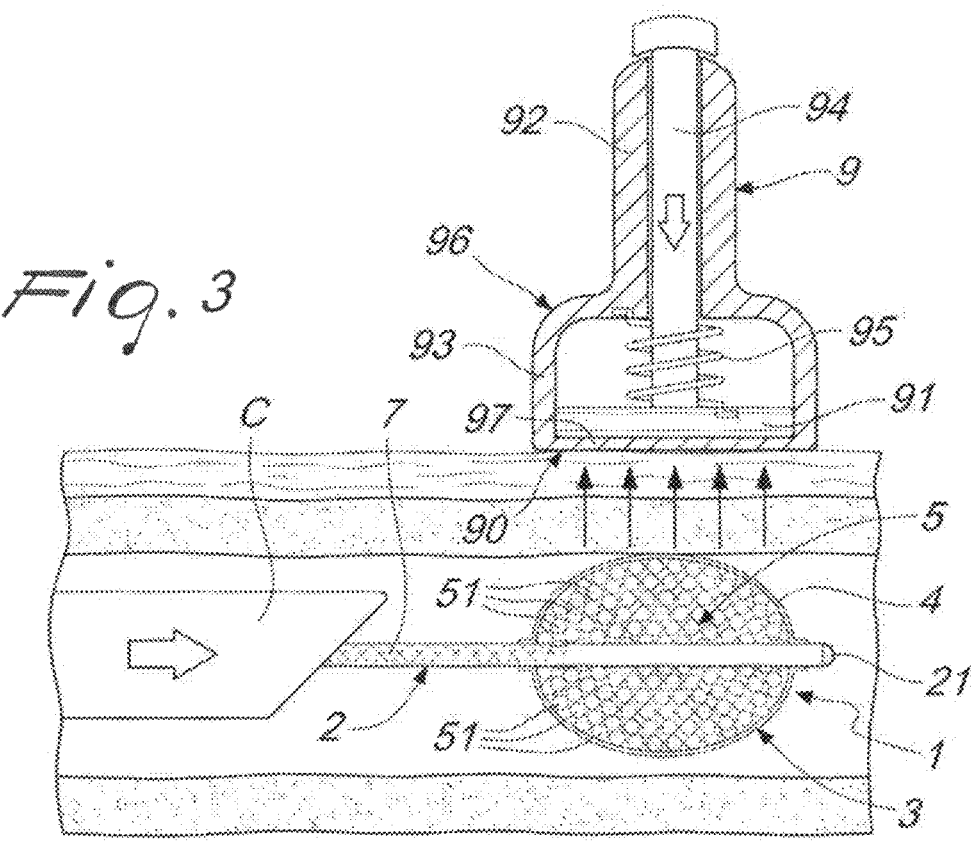
FIG. 3 is a sectional view of the system in FIG. 2, in a second operating condition.
Figure 4:
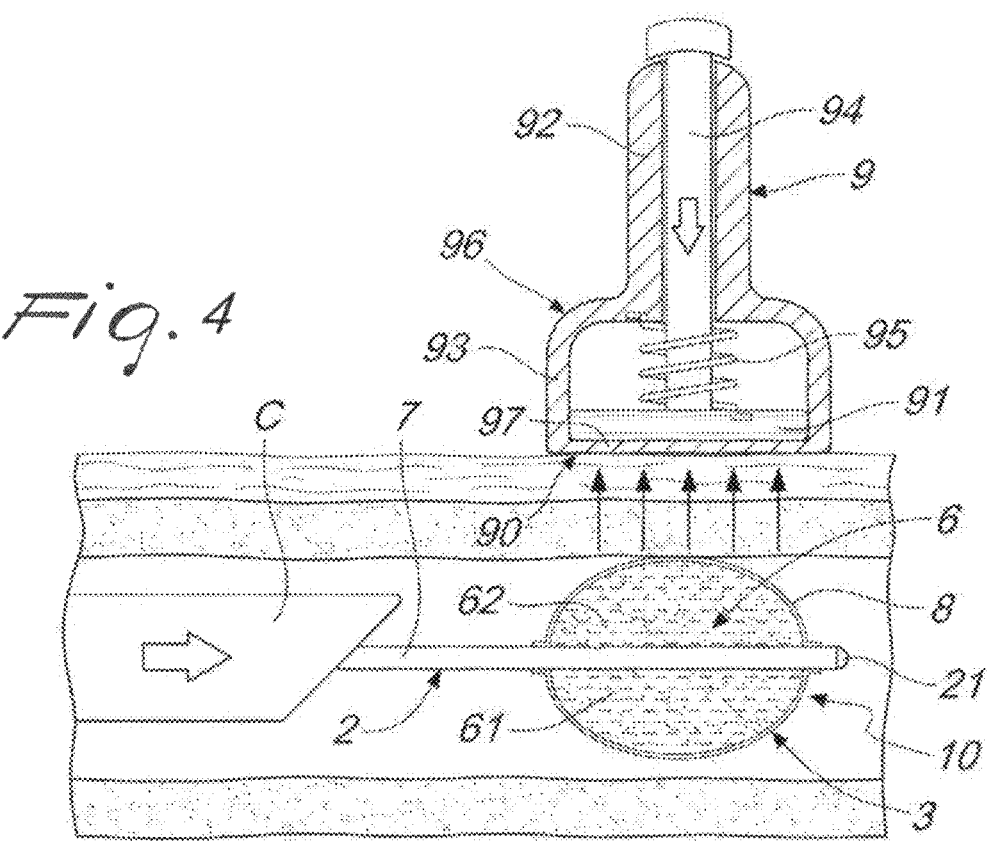
FIG. 4 is a sectional view of a second embodiment of the endoscopy system according to the invention.

The endoscopic guide is indicated, in the first embodiment in FIGS. 1-3, by reference numeral 1, whereas a second embodiment is indicated by reference numeral 10 and is shown in FIG. 4.

In general terms, the endoscopic guide 1, 10 according to the invention comprises a tubular guiding element 2 and an anchoring head 3.

The anchoring head 3 may be placed at or near a terminal end, in particular a distal end, of the tubular guiding element 2, whereas at the other end of the tubular guiding element 2, i.e. at the proximal end, a control device is placed, preferably removably coupled to the tubular guiding element 2.

According to the invention, the tubular guiding element 2 has at least one longitudinal cavity 7 and the anchoring head 3 is provided with at least one container 4, 8 for accommodating a magnetic or ferromagnetic agent 5, 6.

The tubular guiding element 2 is preferably single-lumen (i.e., it accommodates a single longitudinal cavity 7 therein), but in some variants, it has further cavities (for example two cavities, in the case of bi-lumen) for the passage of air, fluids or endoscopic accessories; in this case, it is possible that it comprises a sheath which defines each additional lumen, which sheath may terminate beyond the anchoring head 3.

The container 4, 8 is placed in communication with the longitudinal cavity 7 of the tubular guiding element 2.

In the preferred embodiment, the mutual arrangement of the container 4, 8 and of the tubular guiding element 2 is as shown, i.e. the container 4, 8 is placed near a terminal end (distal end) of the tubular guiding element 2, which passes through the container 4, 8 and projects therefrom with a free guiding end 21.

The length of the free guiding end 21 ranges between a few millimeters and a few centimeters; in the second case, it is preferable that it is soft and flexible so as not to damage the mucosa if the guide is pushed towards the wall of the bowel.

In this embodiment, the container 4, 8 therefore extends peripherally around the tubular guiding element 2 to completely surround it at least by a certain axial length.

In other embodiments (not shown), the container 4, 8 is instead placed to cover the distal end of the tubular guiding element 2, which opens into the container 4, 8.

In yet other embodiments, the shape of the container 4, 8 varies and is subdivided, for example, into radial sectors or segments, like a petal.

The endoscopic guide 1, 10 of the invention further comprises a magnetic or ferromagnetic agent 5, 6 movable in said longitudinal cavity 7 for filling/emptying the container 4, 8.

The term "magnetic or ferromagnetic agent" means any material which reacts to a magnetic field, such as a ferromagnetic or paramagnetic material; this material may be solid, liquid or powdery, it being sufficient that it can be moved inside the longitudinal cavity 7 for filling/emptying the container 4, 8. Preferred embodiments of the magnetic or ferromagnetic agent will be described hereinafter.

Returning briefly to the container 4, 8, in a preferred embodiment, it is manually expandable and retractable, preferably elastically, so as to switch from a retracted condition—in which it is substantially adherent to the body of the tubular guiding element 2—to an expanded condition—in which it protrudes externally from the body of the tubular guiding element 2, and vice versa; the filling or emptying of the container 4, 8 by the magnetic or ferromagnetic agent determines the switching between the retracted and the expanded condition and vice versa.

Turning now to describe the magnetic or ferromagnetic agent 5, according to the first embodiment shown in FIGS. 1-3, it comprises a plurality of magnetizable bodies 51 connected to one another to define a flexible elongated body. Preferably, the flexible elongated body forms a chain, as shown in FIGS. 1-3.

In a different embodiment (not shown), the magnetizable bodies are instead sliding on a common thread which preferably extends at least partially inside the container 4, 8.

In the embodiment shown in FIGS. 1-3, the magnetizable bodies 51 are small metallic spheres, for example made of iron, steel or the like; each sphere is connected to the previous one and the following one by a shaft or a thread, so that each sphere is free to perform a certain degree of rotation with respect to the other spheres: a chain is thus obtained which, by suitably selecting the radius of the spheres, is able to slide into the cavity of the tubular guiding element 2, as shown in FIG. 1, and thus be accommodated in the container 4, as shown in FIGS. 2 and 3.

To this end, it is preferable that the magnetizable bodies 51 have a dimension only slightly smaller than the diameter of the longitudinal cavity 7 of the tubular guiding body 2, so as to freely slide (without deforming the tubular body) therein, thus determining the switching between the retracted and the expanded condition, and vice versa.

In other embodiments (not shown), instead of the spheres, small cylinders are provided which are connected in an articulated manner, similarly to what has just been described.

In yet other embodiments, the shape of the magnetizable elements varies according to the requirements, since elements having different shape and/or dimensions can be placed side by side.

In yet other embodiments, the chain is of the traditional type, for example, with rings, with oval links or the like.

In this embodiment, the container 4 is preferably a mesh bag, either metallic (for example of Nitinol) or plastic; the size of the mesh links must be selected so as to avoid the passage of the chain so that, when the container 4 is full (FIG. 2-3), the chain is prevented from escaping and remains accommodated in the container 4.

The overall length of the flexible element is such that, even in the condition of container 4 full, the chain itself or a connection thereto (not shown) protrude from the side of the guide wire (opposite to that provided with end 21) and terminating for example, with a control device provided at least with a manual or automatic control acting on the chain; this ensures that one can act on the chain to empty the container 4.

It is thus obtained that the operations of filling or emptying the container 4 are particularly easy and quick; at the same time, the mass of magnetic agent which is accommodated in the container 4 is relatively large and contributes to a firm anchoring even if, as shown, the container 4 is selected with maximum dimensions, in expanded condition, such as not to completely occlude the lumen and not to stretch the colic walls, with consequent occurrence of pain and increase of the perforation risk.

By using a mesh container 4, this advantage is amplified, since, even in the case where the maximum dimension of the container 4 is such as to bring it peripherally in complete contact with the walls of the organ lumen, the presence of the mesh and residual interstices between the bodies of the chain leave a certain, albeit small, area of passage for the bodily fluids free.

In the embodiment shown in FIG. 4, the magnetic or ferromagnetic agent 6 comprises a liquid 61 and a plurality of magnetizable bodies 62 in dispersion in said liquid 61; the liquid 61 preferably has only a transport liquid function for bringing the magnetizable particles, normally ferrous particles, into cavity 7 and into/from container 8.

In certain embodiments, the liquid is an aqueous suspension.

In certain embodiments, the magnetizable bodies 62 are ferrous particles dispersed in the liquid and having dimensions ranging from 10 microns to 500 microns.

In certain embodiments, the magnetic or ferromagnetic agent is biocompatible "ferrofluid", preferably comprising nanoparticles and emulsifiers to prevent the particle aggregation.

As regards the container 8, in this embodiment it comprises, or alternatively, consists of, a bag which is hermetic to the passage of liquid 61, in the shape of an inflatable balloon. Examples of inflatable balloons are those normally used in endoscopy, for example nylon balloons or balloons of a polyether-polyamide block copolymer or a compound thereof with a polyamide. Such copolymers and compounds thereof with polyamides are known and have been described in detail in the patent publication WO 2007/132485 A1.

Also in this case it is possible to quickly fill the container, preferably by means of a pump or a plunger (for example a syringe of adequate size) on the liquid to bring it, through the channel 7, into the container 8 or to remove it therefrom; it is then possible to carefully adjust the degree of filling of the container 8, for example by making it reach the maximum dimensions such as not to completely block the lumen of the organ in which it is inserted and not to extend the walls. The degree of filling can be controlled visually through the images transmitted by the endoscope camera.

In this embodiment, a valve is optionally provided between the tubular guiding element 2 and the container 8, adapted to prevent that, when the container 8 is filled with the liquid 61 (i.e., with the magnetizable bodies 62), the latter can flow backwards from container 8 to body 2.

Preferably, to fill the container 8, a syringe or more generally a plunger is used which injects the liquid 61 with the magnetizable bodies 62 into the tubular guiding element 2, through which it reaches the container 8. To this end, the control device is provided at least with an adapter for coupling to said syringe or plunger.

In certain embodiments, both the mesh container 4 and the balloon container 8 are made of elastic material.

The amount of magnetic or ferromagnetic material inserted in the container 4, 8 can be adjusted, not only to determine the dimensions of the container 4, 8 once filled, but also to modulate the force with which the container is held against the wall of the organ in which it is inserted and thus, ultimately, the anchoring force. In particular, the concentration of the powder must be maximized to allow the filling of the balloon with the maximum mass against the smallest possible volumes.

The endoscopy system of the invention comprises an endoscopic guide as described above and a magnetic field source configured to exert a retaining force on the magnetic or ferromagnetic agent 5, 6, with respect to a transverse pulling direction, greater than 3 Newton, or greater than 5 Newton at a distance from 2 centimeters to 10 centimeters.

The expression "exerting a retaining force on the magnetic or ferromagnetic agent 5, 6, with respect to a transverse pulling direction" means the retaining force on the magnetic or ferromagnetic agent with respect to a traction substantially perpendicular to the direction of maximum attraction between magnet and ferromagnetic body, as determined by the lines of force of the magnetic field.

At this point, it is useful to describe how a diagnostic colonoscopy examination is carried out to better understand the invention.

The colonoscope is a flexible endoscope characterized by a tip (about 15 cm long), a body (about 130 cm long) and a manipulator. The tip is movable and the camera, the lights and the orifice of the operating channel are accommodated therein. The tip can be operated by moving the knobs on the manipulator. The body has a flexibility which in some models can also be selected to perform certain endoscopic maneuvers. The cables for the transmission of images, the power supply and the tie rods for connecting the tip to the knobs are accomodated within the body.

The manipulator is characterized not only by the knobs for orienting the tip, but also by the outer orifice of the operating channel and by the controls for the suction or the blowing of air, and the recording of images or videos.

The purpose of diagnostic colonoscopy is to inspect the entire mucosal surface of the colon in order to identify any pathological changes thereof which may require further diagnostic or therapeutic interventions. It is essential that the tip of the colonoscope provided with cameras and lights reaches the last part of the colon called cecum. In fact, should the instrument not reach the cecum, the doctor would not be able to say whether there are any pathological changes in the unexplored tract.

The colon is a hollow tube-shaped movable organ with a lax wall. Unlike other hollow tube organs, such as the arteries, it has a larger diameter, the walls can extend by a few centimeters and the bowel in some segments can be mobilized within the abdominal cavity sometimes even by 30 cm.

These anatomical features prevent the insertion of catheters or guides for stretches greater than 10-30 cm. Catheters, in fact, once inserted into the rectum through the anus, tend to roll up on themselves due to the large diameter of the lumen and to the curves of the bowel. Therefore, contrary to what is done in the vascular field, colon catheterization is difficult to be carried out except for a short stretch. Even in the presence of a radiological check, a catheter or a guide do not have adequate tip mobility or adequate lift. An endoscope or a catheter lift is the ability to transmit the thrust from the instrument body to its tip. The greater the stiffness of an endoscope, the greater the lift. A too rigid endoscope cannot, however, be easily maneuvered along the tortuous path of the colon. The colonoscope is designed to result in a compromise between adequate flexibility and adequate lift.

However, the lift progressively decreases if the colonoscope is in an excessively flexed arrangement. For example, if the colonoscope during a colonoscopy forms a loop, it may no longer be able to transmit the thrust from the body to the tip and therefore the endoscopist cannot make the instrument and its camera advance further. In these cases, if the endoscopist pushes the instrument manually, the result is only the transmission of force on the walls of the bowel, thus causing pain and risk of trauma without being able to advance the tip.

In light of the foregoing, the endoscopic guide 1, 10 of the invention solves the technical problem of introducing the colonoscope up to the cecum, as it allows to implement a method of introducing the colonoscope which comprises the following steps:

a) providing a colonoscope having a distal end, configured to be introduced into a patient's colon, and a proximal end, connected to a maneuver and control manipulator;

b) providing an endoscopy system according to the invention;

c) introducing the distal end of the colonoscope through the patient's anus until a blockage point is reached, i.e. a point beyond which the colonoscope can no longer be advanced;

d) advancing the endoscopic guide 1, 10 up to a given distance beyond the distal end of the colonoscope, where said distance is preferably 4-10 cm;

e) introducing into the container 4, 8 of the endoscopic guide 1, 10 the magnetic or ferromagnetic agent 5, 6, so as to make the container 4, 8 reach an expanded condition;

f) applying an external magnetic field through said magnetic field source at the area of the abdomen in which the expanded container 4, 8 with the magnetic or ferromagnetic agent 5, 6 is present, so as to attract the container 4, 8 against an anchoring point on the wall of the colon with a retaining force on the magnetic or ferromagnetic agent 5, 6, with respect to a transverse pulling direction, greater than 3 Newton, or greater than 5 Newton, or greater than 9 Newton, or about 10 Newton;

g) extending the endoscopic guide 1, 10 by applying a pulling force of at least 3 Newton, or at least 5 Newton on the proximal end of the endoscopic guide 1, 10;

h) advancing the colonoscope to the anchoring point of the container 4, 8;

i) optionally, emptying container 4, 8 of the magnetic or ferromagnetic agent 5, 6;

l) repeating steps d) to i) until an anchoring point at the cecum is reached.

It is important that the endoscopic guide has a sufficiently wide lumen to allow the quick and easy sliding of the magnetic or ferromagnetic agent 5, 6, in particular when said agent consists of an aqueous suspension of ferromagnetic particles, having a high viscosity (high concentration and use of heavy particles) and tendency to form clots and to settle and thus occlude the guide channel. To this end, the tubular guiding body 2 of the endoscopic guide 1, 10 of the invention preferably has a diameter from 2 to 3.5 mm, depending on the diameter of the operating channel of the colonoscope which is generally between 2.8 and 3.8 mm, depending on its use. The inner diameter of the lumen of the tubular guiding body 2 will therefore be of at least 1 mm, for example between 1 mm and 3 mm.

The endoscopic guide 1, 10 in step d) can be made to slide inside the lumen of the colonoscope or in a separate outer channel parallel to the colonoscope, which must be introduced before colonoscopy. The advantage of using this separate channel for the endoscopic guide 1, 10 is to keep the endoscope lumen free, so as to be able to introduce other instruments therein, such as suture needles or devices for cutting and removing polyps or similar formations. If, on the other hand, the lumen of the colonoscope is used for the introduction of the endoscopic guide 1, 10, it must be retracted once the position of maximum introduction has been reached, in order to make the diagnostic examination and, if necessary, surgery on the possible lesion, easier.

Even when a separate channel for the endoscopic guide 1, 10 is used, this still acts as a guide for the colonoscope, as the latter can be held adjacent to the guide during introduction.

As mentioned above, a preferred embodiment provides for the use of a ferromagnetic fluid as a ferromagnetic agent 6. Such a ferromagnetic fluid is preferably an aqueous suspension of iron powder, magnetite or maghemite, i.e. is based on iron oxides. In certain embodiments, the so-called "ferrofluid" is used, which is a suspension of iron oxides in the form of nanoparticles coated with a surfactant to prevent the agglomeration thereof. The aqueous suspension of ferromagnetic agent of the invention is generally a suspension of 30% to 70% vol/vol, preferably about 50% vol/vol, of said iron oxides in water, where preferably the iron oxides have a particle size from 10 nanometers to 500 microns, or from 1 micron to 500 microns, more preferably from 1 micron to 200 microns, even more preferably from 1 micron to 50 microns, most preferably from 1 micron to 20 microns.

In other embodiments, the magnetic or ferromagnetic agent comprises an aqueous suspension of magnetic or ferromagnetic particles wherein an amount equal to or less than 50% by weight comprises or is made of particles having a particle size less than 100 nanometers and, in some embodiments, the aqueous suspension contains an amount equal to or less than 50% by weight of particles having a particle size less than 100 nanometers and an amount equal to or less than 10% by weight of particles having a particle size greater than 1 micron, the remaining part being particles having a particle size from 100 nanometers and 1 micron. In another embodiment, the magnetic or ferromagnetic agent comprises an aqueous suspension of magnetic or ferromagnetic particles having a bimodal particle size distribution with a first peak below 1 micron and a second peak above 1 micron. The particle size of the magnetic or ferromagnetic particles can be determined by known methods, such as:

direct observation by means of electron microscopy;

determination with laser light scattering methods on the aqueous suspension, using a laser granulometry analyzer (Malvern Mastersizer 3000) with LALLS (Low Angle Laser Light Scattering) technique using the Fraunhofer calculation theory.

The expanded container 4, 8 has a volume such as not to occlude the lumen of the colon, which ranges according to the stretches between 3 and 7 cm. Therefore, the volume of the expanded container 4, 8, in particular the volume of the expanded balloon 8, is between 15 and 200 mL, preferably between 20 and 40 mL. This volume corresponds to the volume of the ferromagnetic fluid 6 introduced therein.

The retaining force of the container 4, 8 against the wall of the colon, with respect to a transverse pulling direction, which, as said, must be greater than 5 Newton to allow an adequate traction of the endoscopic guide 1, 10 in step g), depends on the applied magnetic field, which in turn depends on the distance at which a magnetic field source is located from the container 4, 8 filled with the ferromagnetic agent 6. Normally, such a distance is from 2 to 5 cm in most of the colon segments. In obese patients, however, this distance will be greater, for example up to 10 cm. The magnetic field source will thus be selected according to the type of use of the instrument and the type of patient. For the purposes of the invention, it will be possible to use a magnetic field equivalent to that generated by a permanent discoid magnet with magnetization N45 (i.e. a magnet in which the maximum magnetic energy per volume which can be stored in the magnet is 45 Mega-Gauss-Oersted) having a diameter from 50 to 80 mm and thickness from 30 to 60 mm. If a permanent magnet is used, it can be made of sintered Neodymium, sintered ferrite, plastoneodymium or the like.

In preferred embodiments, step f) of magnetic field application can be carried out by applying such a magnetic field progressively. In fact, if the necessary magnetic field were applied very quickly, this would cause a sudden displacement of the container 6, which could therefore cause a sudden and painful stretching of the patient's bowel. The progressive application of the magnetic field can be obtained in two ways:

f1) increasing the applied magnetic field by progressively varying the distance of the magnetic field source and/or the intensity of the magnetic field, or f2) progressively introducing aliquots of ferromagnetic agent 6 into the container 8 with already applied magnetic field.

The introduction of the ferromagnetic fluid 6 in step e) according to the invention can take place either by means of a special pump or simply by means of a syringe which, to this end, will have a volume from 15 to 200 mL, preferably from 20 to 40 mL. Similarly, the container 4, 8 can be emptied in step h).

The step g) of pulling the endoscopic guide 1, 10 has the purpose of keeping the guide tensioned, thus allowing an easier sliding of the endoscope, and at least in part reducing the curvature of the colon loops, also in this case to promote the introduction of a relatively rigid endoscope.

As regards instead the overall length of the tubular element 2 of the endoscopic guide 1, 10 of the invention, it is preferably such as to allow the replacement of a catheter with another catheter, for example a different type of catheter, during the operation. Generally, the tubular element 2 has a length from 2.5 to 4 meters.

Turning now to a particular embodiment of the endoscopy system comprising an endoscopic guide according to the invention, it comprises an endoscopic guide 1, 10 of the type just described and a magnetic handpiece 9, shown in the accompanying FIGS. 2-4.

The magnetic handpiece 9 is designed to be positioned outside the patient's body and, operated by an operator, it can interact with the endoscopic guide 1, 10 which is instead, during the analysis, inside the patient's body. The magnetic handpiece 9 described herein may also be used, per se, to operate various endoscopic devices such as a capsule, an endoscope, a guidewire or the like, which to this end must be provided with a magnetic or magnetizable portion.

In certain embodiments, the magnetic handpiece 9 comprises a magnetic field source 91, a handle portion 92 and an operating end 90.

The operating end 90 consists of that portion of the handpiece 9 which, in use, is close to or in direct contact with the patient's body, in the vicinity of the area where endoscopy is performed (for example, the abdomen for colonoscopy, etc.).

In certain embodiments, the magnetic field source 91 is movable with respect to the operating end 90 of the handpiece 9 between a working position and a safety or rest position, in which:
  in the working position, the magnetic field source 91 is close to the operating end 90,
  in the safety or rest position, the magnetic field source 91 is remote from the operating end 90.

Since the magnetic field source 91 generates the magnetic field and since the latter acts with different intensity as a function of its distance from a cooperating magnetic or ferromagnetic agent of the endoscope, in particular of the endoscopic guide 1, 10, it follows that bringing the magnetic field source 91 to the working position has an appreciable effect of the magnetic field on the magnetic or ferromagnetic agent 5, 6, essential for anchoring, moving and/or orienting the endoscope (and/or the components thereof) and/or the guidewire of the endoscope.

In the preferred embodiment illustrated in the figures, the magnetic handpiece 9 comprises a housing casing 96 ending on one side with or at the operating end 90; on the opposite side, the casing 96 is connected to the handle portion 91, so that the operator can easily handle the handpiece 9.

In the preferred embodiment, the magnetic handpiece 9 does not have support structures articulated to the handpiece 9, which is then gripped and moved freely in space by the operator.

The housing casing 96 accommodates the magnetic field source 91 therein at least at the working position, preferably also at the safety or rest position, as in the example in the accompanying figures.

In one embodiment, in the rest position the magnetic field source 91 is accommodated at or within the handle portion 92; thereby, there is a greater movement stroke of the magnetic field source 91 between the two limit positions, rest and working, with respect to the situation shown in which the magnetic field source 91 moves only between the two limit positions within casing 96, corresponding to the working and rest positions.

In a different embodiment (not shown), the magnetic field source 91 is accommodated in one side of the handpiece 9 in working condition and in the opposite side in the rest condition. To this end, an additional housing casing is provided, located on one side of handle 92 opposite to that connected to casing 96: the magnetic field source 91 moves from the working position (in which it is accommodated within casing 96) to that of safety and rest (in which it is accommodated within the additional casing) and vice versa, preferably passing into the handle portion 92.

The casing 96 and possibly the additional casing (if provided) can also be made in one piece with the handle portion 92.

As regards the means for determining the displacement of the magnetic field source 91, it should be noted that, in one embodiment, the working position is an unstable equilibrium position, i.e. a position in which the magnetic field source 91 remains only under the action of a control force. This introduces an additional intrinsic safety factor to the handpiece 9 of the invention: if the action of the control force ceases, the magnetic field source 91 will no longer remain in the working position, thus preventing possible drawbacks.

To this end, preferably, the handpiece 9 comprises return means 95 designed to bring the magnetic field source 91 from the working position to the safety or rest position and/or a pusher element 94 acting with a control force on the magnetic field source 91 to move it between the rest or safety position and the working position in an antagonistic manner to the return means 95.

The pusher element 94 is configured to be operated by the operator, for example manually, by means of a special control end, for example in the form of a button which the operator actuates, for example with his/her thumb, when he/she holds the handpiece 9.

When the action of the control force on source 91 ceases, it returns to the safety or rest position by means of the return means 95 which in the preferred embodiment, are elastic return means 95 and comprise a return spring.

It should be noted that variants to what has been described thus far are possible, for example the return means 95 may comprise elastomers or in turn be magnetic return means in which the magnetic field source 91 is returned to the rest or safety position due to a local magnetic field of sufficient magnitude to exert a return action of the magnetic field source 91, but not such as to negatively affect the magnetic field generated by the latter and adapted to control the endoscopic system or the parts thereof.

In a variant of the handpiece, the means for determining the displacement of the magnetic field source 91 are implemented by means of a screw system (not shown), which allows adjustment and maintenance at a given position of the magnetic field source 91. In practice, the magnetic field source 91 is fixed to a screw element which in turn is coupled to a threaded hole arranged on the casing 96, such that, by screwing or unscrewing the screw element, the lowering or the raising of the magnetic field source is obtained.

In preferred embodiments, the magnetic field source 91 is a permanent magnet, as shown in the figures and as described above. In this case, the magnetic field generated by the magnetic field source 91 remains even when the latter is in rest or safety position; to improve the functionality of the handpiece 9 in this condition it is preferable to provide shielding elements of the magnetic field, active when the magnetic field source 91 is in the safety or rest position.

Such shielding elements of the magnetic field can be implemented in various known manners, according to the requirements.

In a first example, the shielding elements of the magnetic field comprise ferromagnetic shield elements, which deflect the magnetic field force lines such that, when the magnetic field source 91 is in the safety position, the magnetic field generated thereby and directed towards the operating end 90 is irrelevant or close to zero or zero.

In another example, the shielding elements of the magnetic field comprise conductive shields in which currents are generated which create a local magnetic field which is added to that of the magnetic field source 91 so as to obtain effects similar to those described above.

In another example, the two types of shielding elements are combined with each other, therefore both ferromagnetic shield elements and conductive shields are present.

In other embodiments not shown, the magnetic field source 91 consists of or comprises an electromagnet.

In this case, since the electromagnet is electrically powered for the generation of the magnetic field, it is sufficient that, when the magnetic field source 91 is in rest or safety condition, the electromagnet is not powered or at least it is with a current less than the power supply in working condition.

In certain embodiments (not shown), when the magnetic field source 91 is or comprises an electromagnet, the transition from a working condition to a rest or safety condition does not require displacement from a position close to the operating end 90 to a remote position therefrom. In such embodiments, the electromagnetic field source 91 is fixed and placed near the operating end 90 of the handpiece 9 and can be activated (working condition) or deactivated (rest or safety condition) by acting on a special switch, for example a pressure switch, placed in an ergonomic position on the handpiece 9, or on a release button.

Returning to other optional features of the handpiece 9 of the invention, the housing casing 96 is closed by an end wall 97 at the operating end 90; this prevents the magnetic field source 91 from coming into direct contact with the patient's skin and/or requiring sterilization of the interior of casing 96 at the end of each use. To this end, the wall 97 is sealably coupled or made in one piece with the casing 96, for example with the skirt wall 93 of the latter.

In certain embodiments, the system according to the invention comprises a device for detecting the distance between the magnetic field source 91 and the container 4, 8. In practice, the container 4, 8 or the tip of the endoscopic guide 1, 10 comprise a passive sensor, for example of the RFID type, whereas the magnetic field source 91 is associated with a distance sensor configured to detect the distance of the passive sensor. This device may comprise an audible warning device and/or a system for blocking the advancement of the magnetic field source. This device therefore implements a safety system to prevent an excessive attraction force from being exerted on the container 4, 8 (which force, as is known, is inversely proportional to the distance between magnet and attracted body), with consequent damage to the walls of the patient's organ.

As will be understood from the above description, the use of a handpiece 9, however preferable, is not indispensable for the correct use of the endoscopic guide of the invention. In fact, the magnetic field source can be positioned in a plate or other instrument fixed above the bed on which the patient is placed or movable above it in a manual or automatically controlled manner. For example, the magnetic field source, either permanent or electromagnetic, can be connected to a movable arm, for example an articulated arm, which can be brought into the working condition by maneuvering it manually or by controlling its movements through electric actuators or even in automatic manner, based on a pre-selected operating program.

The invention further relates to an endoscopy kit, comprising an endoscopic guide 1, 10 according to the invention, a container of a ferromagnetic fluid in a predetermined amount, optionally a catheter, optionally a handpiece comprising a magnetic field source as described above, optionally a syringe connectable to the endoscopic guide of the invention to introduce a ferromagnetic fluid.

In certain embodiments of the kit of the invention, the syringe is preloaded with a suspension of said ferromagnetic fluid 6 as described above, preferably in a volume ranging from 15 to 200 mL, more preferably from 20 to 40 mL.

In practice, it has been found that the invention meets the intended tasks and purposes, as it allows to have an endoscopic guide, in particular for colonoscopes, which allows the diagnostic analysis or the surgical removal of a lesion of the colon to be carried out quickly and completely, since it is possible to insert the colonoscope up to the maximum point at the cecum by pulling the guide. Such a traction is allowed by the strong anchoring obtainable with the guide of the invention, which in turn is the result of the considerable amount of ferromagnetic agent which can be introduced into the balloon 8 and of the high magnetic field applicable from the outside through the handpiece or other source of magnetic or electromagnetic field.

Moreover, the endoscopic guide 1, 10 allows to carry out at least small displacements of the anchoring head (container 4, 8) even when the latter is in the locking position: to this end, in fact, the operator can use the external magnetic field to move the anchoring head to a suitable position.

Furthermore, the operator has an endoscopic guide which only requires support at a limited area of the lumen of the organ in which it is introduced to ensure a stable fixing, therefore without the need to occlude the entire lumen.

Last but not least, it is noted that the endoscopic guide and the system comprising such a guide are relatively quick to be operated, as well as being relatively cost-effective and simple to be implemented.

Finally, the guide and the system are relatively safe even in case of malfunctions during the examination.

A further advantage of the invention is related to the possibility of more precisely locating a lesion, for example in the case of colonoscopy: in fact, it is possible to locate (topographically) on the patient's abdomen the point where a lesion of the colon is located. In fact, in use, the external handpiece is magnetically hooked to the head of the guide at the point of the abdominal surface closest to the anchoring head, which can be advantageously used to highlight where a lesion is located relative to the abdominal surface.

It is apparent that only some particular embodiments of the present invention have been described, and those skilled in the art will be able to make all the required modifications for its adaptation to particular applications, without departing from the protection scope of the present invention.

In the practice, the materials used as well as sizes and shapes may be changed according to the requirements and the progress of the technics, provided that they are compatible with the specific use.

What is claimed is:

1. An endoscopic guide comprising:
   a proximal end,
   a distal end,
   a tubular guiding element comprising:
     a body comprising a single lumen having an inner diameter of at least 1 mm,
     a longitudinal cavity,
     an anchoring head comprising an endoscopic balloon configured to accommodate a magnetic or ferromagnetic agent, the endoscopic balloon expandable and retractable between a retracted condition, in which the endoscopic balloon is adherent to the body of the tubular guiding element, to an expanded condition, in which the endoscopic balloon protrudes externally from the body of the tubular guiding element, the endoscopic balloon being in communication with the longitudinal cavity of the tubular guiding element, and
     a magnetic or ferromagnetic agent movable in the longitudinal cavity of the tubular guiding element and configured to fill and empty the endoscopic balloon, the magnetic or ferromagnetic agent comprising a liquid and a plurality of magnetizable bodies in dispersion in the liquid, the expanded condition of the expandable balloon corresponding to a volume of the magnetic or ferromagnetic agent contained therein; and
   a magnetic field source comprising a permanent magnet, the magnetic field source configured to generate a magnetic field equivalent to that generated by a permanent discoid magnet with N45 magnetization having a diameter between 50 mm and 80 mm and a thickness between 30 mm and 60 mm to exert a retaining force on the magnetic or ferromagnetic agent contained in the endoscopic balloon, with respect to a transverse pulling direction, greater than 3 Newton at a distance between 2 cm and 10 cm when a pulling force of at least 3 Newton is applied on the proximal end of the endoscopic guide.

2. The endoscopic guide according to claim 1, wherein the magnetic field source is configured to exert a retaining force on the magnetic or ferromagnetic agent contained in the endoscopic balloon greater than 5 Newton.

3. The endoscopic guide according to claim 1, wherein the magnetic or ferromagnetic agent comprises an aqueous suspension of magnetite or maghemite or a ferrofluid, and wherein the magnetic or ferromagnetic agent comprises a suspension of 30% to 70% vol/vol of iron oxides in water.

4. The endoscopic guide according to claim 3, wherein the iron oxides have a particle size from less than 10 nanometers to 500 microns.

5. The endoscopic guide according to claim 3, wherein the iron oxides have a particle size from 1 micron to 500 microns.

6. The endoscopic guide according to claim 3, wherein the iron oxides have a particle size from 10 microns to 500 microns.

7. The endoscopic guide according to claim 3, wherein the iron oxides have a particle size from 1 micron to 200 microns.

8. The endoscopic guide according to claim 3, wherein the iron oxides have a particle size from 1 micron to 50 microns.

9. The endoscopic guide according to claim 3, wherein the iron oxides have a particle size from 1 micron to 20 microns.

10. The endoscopic guide according to claim 1, wherein the magnetic or ferromagnetic agent comprises an aqueous suspension of magnetic or ferromagnetic particles wherein an amount equal to or less than 50% by weight is made of particles having a particle size less than 100 nanometers.

11. The endoscopic guide according to claim 10, wherein the aqueous suspension contains an amount equal to or less than 10% by weight of particles having a particle size greater than 1 micron, the remaining part being particles having a particle size from 100 nanometers and 1 micron.

12. The endoscopic guide according to claim 1, wherein the magnetic or ferromagnetic agent comprises an aqueous suspension of magnetic or ferromagnetic particles having a bimodal particle size distribution with a first peak below 1 micron and a second peak above 1 micron.

13. The endoscopic guide according to claim 1, wherein the permanent magnet comprises sintered Neodymium, sintered ferrite, or plastoneodymium.

14. The endoscopic guide according to claim 1, wherein the magnetic or ferromagnetic agent comprises an emulsifier.

15. The endoscopic guide according to claim 1, wherein the inner diameter of the lumen of the body of the tubular guiding element is between 1 mm and 3 mm.

16. The endoscopic guide according to claim 1, wherein the distance is between 4 cm and 10 cm, wherein the expanded volume of the balloon is between 15 mL and 200 mL.

17. The endoscopic guide according to claim 1, wherein the diameter of the body of the tubular guiding element is between 2 mm and 3.5 mm.

18. The endoscopic guide according to claim 1, wherein the magnetic field source is configured to exert a retaining force on the magnetic or ferromagnetic agent contained in the endoscopic balloon greater than 9 Newton.

19. The endoscopic guide according to claim 1, wherein the magnetic field source is configured to exert a retaining force on the magnetic or ferromagnetic agent contained in the endoscopic balloon greater than 10 Newton.

20. The endoscopic guide according to claim 1, wherein the distance is between 4 cm and 10 cm, wherein the expanded volume of the balloon is between 20 mL and 40 mL.

21. An endoscopy kit, comprising an endoscopic guide according to claim 1, a container of a ferromagnetic fluid in a predetermined amount apt to fill the balloon of the endoscopic guide to a volume between 15 mL and 200 mL, a catheter, a handpiece comprising the magnetic field source, a syringe connectable to the endoscopic guide to introduce the ferromagnetic fluid, wherein the syringe is prefilled with said ferromagnetic fluid to constitute the container.

* * * * *